United States Patent
Abraham-Fuchs et al.

(10) Patent No.: US 7,572,284 B2
(45) Date of Patent: Aug. 11, 2009

(54) METHOD FOR AUTOMATED LOCALIZATION OF LESIONS IN THE GASTROINTESTINAL TRACT FOR TREATMENT USING LASER LIGHT FROM AN ENDOROBOT

(75) Inventors: Klaus Abraham-Fuchs, Erlangen (DE); Friedrich Fuchs, Roettenbach (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 944 days.

(21) Appl. No.: 10/958,294

(22) Filed: Oct. 6, 2004

(65) Prior Publication Data

US 2005/0096712 A1    May 5, 2005

(30) Foreign Application Priority Data

Oct. 6, 2003   (DE) ............................... 103 46 276

(51) Int. Cl.
*A61N 5/067* (2006.01)
(52) U.S. Cl. ............................ 607/92; 607/88; 607/89
(58) Field of Classification Search .................. 607/88, 607/89, 92; 128/898; 600/109, 117, 160, 600/178, 424, 425, 427
See application file for complete search history.

(56) References Cited

U.S. PATENT DOCUMENTS 5,993,378 A * 11/1999 Lemelson .................. 600/109
6,240,312 B1 * 5/2001 Alfano et al. ............... 600/476
2001/0051766 A1   12/2001 Gazdzinski
2003/0060702 A1 * 3/2003 Kuth et al. .................. 600/424
2005/0090711 A1 * 4/2005 Fuchs et al. ................. 600/113
2005/0192478 A1 * 9/2005 Williams et al. ............ 600/160
2005/0192660 A1 * 9/2005 Abraham-Fuchs et al. . 623/1.11
2005/0267414 A1 * 12/2005 Abraham-Fuchs et al. .. 604/173
2005/0273139 A1 * 12/2005 Krauss et al. ............... 606/221

FOREIGN PATENT DOCUMENTS

DE           10161958 A1     7/2003

OTHER PUBLICATIONS

European Office Action dated Jan. 17, 2005.

* cited by examiner

*Primary Examiner*—Ahmed M Farah
(74) *Attorney, Agent, or Firm*—Harness, Dickey & Pierce, P.L.C.

(57) ABSTRACT

A method is for automated localization of lesions in the gastrointestinal tract using laser light from an endorobot. The method includes recording of surface images of the gastrointestinal tract using the camera of the endorobot. Next, the surface images are transmitted to a computer. The surface images are then analyzed by the computer on the basis of lesion-specific features with regard to lesions to be irradiated. Thereafter, control signals are computed by the computer on the basis of a detected lesion, and the control signals are transmitted to an endorobot steering device and/or to a laser system located in the endorobot. Finally, the computed laser-beam orientation and size of the laser irradiation area are adjusted by the endorobot steering device and/or by the laser system, on the basis of the control signals.

32 Claims, 2 Drawing Sheets

METHOD FOR AUTOMATED LOCALIZATION OF LESIONS IN THE GASTROINTESTINAL TRACT FOR TREATMENT USING LASER LIGHT FROM AN ENDOROBOT

The present application hereby claims priority under 35 U.S.C. §119 on German patent application number DE 103 46 276.7 filed Oct. 10, 2003, the entire contents of which are hereby incorporated herein by reference.

FIELD OF THE INVENTION

The present invention relates generally to endoscopy using an endorobot for performing minimally invasive diagnoses and interventions inside the body, preferably in the gastrointestinal tract of a patient. More particularly, it relates in particular to a method and a system for implementing the method for quickly identifying lesions and irradiating them with laser light independently of the operator.

BACKGROUND OF THE INVENTION

The human gastrointestinal tract (stomach-intestine tract) is a setting for acute and/or chronic diseases, for example in the form of pathologically altered areas on the internal wall of the stomach or intestine that bleed sporadically or continuously, for example as part of inflammatory or neoplastic processes.

Of particular importance are inflammatory intestinal diseases such as Crohn disease, Ulcerative Colitis, neuroendocrine tumors of the small intestine, tumors in general or else even small tissue alterations such as polyps, the majority of which degenerate malignantly over time. Often these pathological tissue alterations, referred to below as (superficial) lesions, appear in many places in the same patient and normally develop into malignant intestinal cancers if their growth is not stopped early enough by removal or other means of destruction, for example by electrocoagulation or coagulation by means of laser light.

This destruction of the aforementioned lesions by coagulation is performed according to the state of the art by use of an endoscope or an endorobot. An endorobot having a laser suitable for ablation is described in the U.S. Pat. No. 6,240,312 B1. The navigation of such an endorobot inside the body is implemented by a magnetic-field steering system by use of an endorobot steering device and is presented in detail in the patent DE 101 42 253 C1.

SUMMARY OF THE INVENTION

Owing to the enormous length of the intestine (up to 11 meters) and the usually large number of lesions, it is an object of an embodiment of the present invention to provide a method and a system by which lesions in the gastrointestinal tract can be detected automatically and destroyed or treated by automatic device(s).

According to an embodiment of the invention, a method for automated localization of lesions in the gastrointestinal tract using laser light from an endorobot includes:

recording of surface images of the gastrointestinal tract using the camera of the endorobot, transmission of the surface images to a computer, analysis of the surface images by the computer on the basis of lesion-specific features with regard to lesions to be irradiated, computation of control signals by the computer on the basis of a detected lesion, transmission of the control signals to an endorobot steering device and/or to a laser system located in the endorobot, and adjustment of the computed laser-beam orientation and size of the laser irradiation area by the endorobot steering device and/or by the laser system on the basis of the control signals.

In addition, a method is claimed according to an embodiment of the invention that enables a controlled irradiation of the detected lesion, comprising the following steps:

irradiation using the laser of the endorobot of the lesion detected by the computer on the basis of lesion-specific features, measurement of current lesion-specific features of the irradiated area by the camera after switching off the laser calculation of the size of the laser irradiation area by the computer on the basis of the measured current lesion-specific features, setting up the calculated size of the laser irradiation area by positioning the endorobot orthogonally to the lesion surface, and continuous or pulsed irradiation of the lesion surface, measurement and monitoring of the size and the current lesion-specific features of the laser irradiation area on the lesion surface.

In an embodiment of the invention, the size of the laser irradiation area is also advantageously varied as a function of the measured current lesion-specific features of the laser irradiation area on the lesion surface by adjusting the distance of the endorobot from the lesion surface.

In another embodiment of the invention, the size of the laser irradiation area is varied as a function of the measured current lesion-specific features of the laser irradiation area on the lesion surface by varying the laser system.

According to an embodiment of the invention, the lesion-specific features concern the color, the shape and the texture of a specific lesion.

The lesion-specific features are advantageously compared with lesion features in a library accessible to the computer or in a library of the computer.

According to an embodiment of the invention, the irradiation with laser light can be interrupted or stopped at any time or at periodic intervals in order to measure the size of the laser irradiation area and to measure the lesion-specific features.

The recording of surface images, the transmission to the computer and the analysis by the computer are advantageously performed continuously.

In another embodiment of the invention, the whole lesion surface is irradiated with a defined surface power density of the laser by transverse displacement of the laser beam in the XY-plane or by tilting the laser beam relative to the lesion-endorobot connecting line (Z-axis) by suitable movement of the endorobot in combination with the supervised positioning in the Z-direction of the endorobot.

According to an embodiment of the invention, the surface power density is in this case defined by the computer over time as a function of the type of the lesion.

The transverse displacement of the laser beam in the XY-plane and/or the tilting of the laser beam relative to the Z-axis is advantageously performed by three-dimensional orientation of the laser relative to the endorobot.

In this case, the three-dimensional orientation of the laser relative to the endorobot is performed in a possible embodiment by miniaturized electromechanical mechanisms such as movable membranes, shape memory alloys, electrically contractile polymers, piezo-actuators etc.

In another embodiment of the invention, the movement of the laser beam is effected by moving a screen.

In yet another embodiment of the invention, the movement of the laser beam is effected by actuating selected laser diodes of a 3D laser diode array integrated in the endorobot.

In still another embodiment of the present invention, the movement of the laser beam is effected by a magnetic-field steering system, in which the laser integrated in the endorobot is coupled to a movable miniature magnet or magnetizable material that is not used for navigation of the endorobot and that can be tilted and/or displaced by applying an external magnetic field.

An orientation of additional components of the endorobot, for example the camera, is performed in another embodiment of the invention by way of the steering principles.

In addition, another embodiment includes a system for implementing a method according to an embodiment of the invention.

In possible embodiments of the system, the computer can either be outside the patient or else integrated in the endorobot or else constitute a combination of integrated and externally located computers.

Further advantages, features and properties of the present invention are now described in more detail from exemplary embodiments with reference to the accompanying drawings.

BRIEF DESCRIPTION OF THE DRAWINGS

The present invention will become more fully understood from the detailed description of the exemplary embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
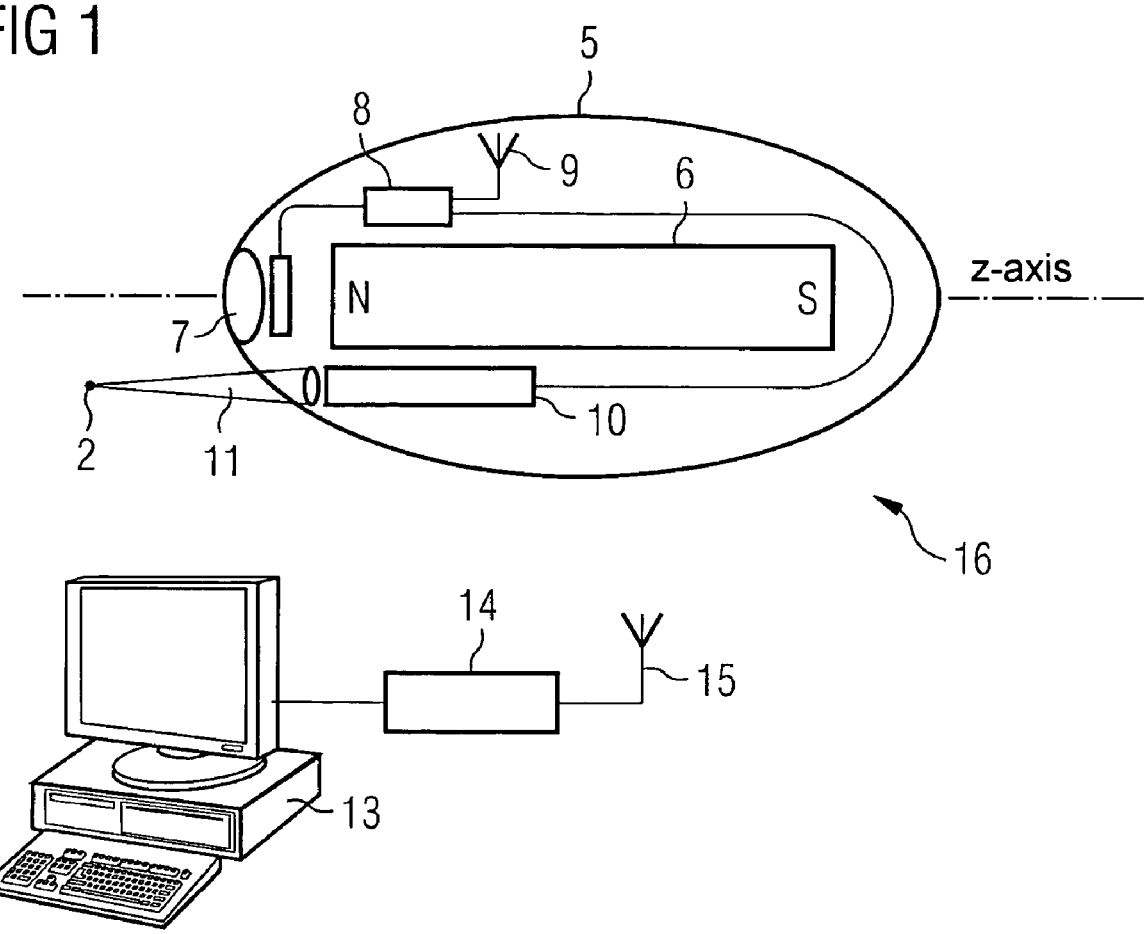
FIG. 1 shows a system with which the laser beam of an endorobot can be maneuvered under computer control.

FIG. 1 shows an endorobot 5 including a laser 10 suitable for ablation. The emanating laser beam 11 is collimated and focused parallel to the lesion-endorobot connecting line (referred to below as the Z-axis). The laser focal point 2 is normally located a few centimeters away from the endorobot 5. A (CCD) camera 7 with lens system is arranged centrally at the laser-beam end of the endorobot 5, by which the part of the laser beam 11 on the focal-point side can be detected optically. The camera 7 is connected to an RF transmit and receive unit 8 by which the recorded images are transmitted in real time via an antenna 9 of the endorobot to the RE transmit and receive unit 14 of a computer 13 via an antenna 15. The transmitted images can be displayed, for example, on the screen of the computer and used by the user (e.g. the doctor) for diagnosis or treatment planning.

The endorobot is here steered or maneuvered in the gastrointestinal tract via a magnetic-field steering system (not shown). The endorobot is provided with a linear magnet 6 for this purpose, on which a torque and a translation force can be exerted in interaction with a 3D gradient field so that the endorobot is moved along the intestine for example. In one option, the endorobot is navigated by the user using a force input device (e.g. a 6D mouse as it is known) by which the 3D gradient field can be suitably varied. Another option would be computer-controlled navigation, in which the computer detects the intestinal wall via the camera of the endorobot and steers or controls the 3D gradient field so that the endorobot is guided along the intestine independently of the user.

An embodiment of the present invention thus involves designing the endorobot computer system so that the endorobot detects lesions in the intestinal wall via the camera and irradiates them in such a way using its laser substantially independently of the user that these lesions can ultimately be considered treated. One of the main points of an embodiment of the invention is the automation of the irradiation following prior identification, also performed automatically, of the lesion concerned.

The system according to an embodiment of the invention includes first a capsule-like endorobot 5 that includes a bar magnet 6, a camera 7 and a laser 10 suitable for ablation. The bar magnet 6 is coupled electromagnetically to dynamic magnetic fields of a magnetic-field steering system as part of an endorobot steering device allowing the endorobot 5 to be navigated in three dimensions e.g. using a 6D mouse. The dynamic magnetic fields are generated by Maxwell coils arranged around the patient under examination. Camera 7 and laser 10 of the endorobot 5 are connected to an RF transmit and receive unit 8 of the endorobot 5, the transmit and receive unit being connected to an antenna 9. The system 16 also includes a computer with screen 13. The computer 13 is also connected to an RF transmit and receive unit 14, which in turn is connected to an antenna 15, so that in particular the images recorded (continuously) by the endorobot camera 7 can be sent to the computer 13 and displayed on its screen in real time. Based on the image displayed on the screen of the computer 13, the endorobot 5 is oriented or positioned accordingly by the user and the laser 10 adjusted accordingly.

Figure 2:
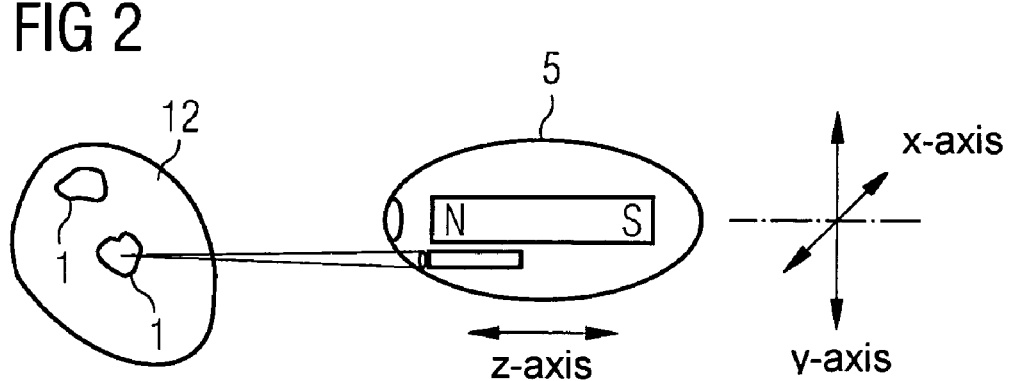
FIG. 2 shows in a Cartesian coordinate system relative to a lesion to be coagulated of a diseased organ surface, an endorobot including a laser.

FIG. 2 shows a rough sketch of the irradiation procedure. The camera 7 of the endorobot detects a lesion 1 on the diseased organ surface 12, for example the intestine surface. In an advantageous embodiment of the invention, detection of a lesion 1 is computerized and is explained in more detail later. The computer 13 acts on the endorobot 5 via the magnetic-field steering system so that the laser beam 11 is directed onto the detected lesion 1 by tilting the endorobot 5 and/or displacing it in the X- and Y-direction. The size of the laser irradiation area and hence the surface power density of the irradiation can be adjusted or set by displacing the endorobot 5 along the lesion-endorobot connecting line (Z-axis).

The aforementioned initial orientation of the endorobot 5 by the computer and the subsequent computer-controlled irradiation itself is performed according to an embodiment of the invention automatically in interaction with the camera 7 integrated in the endorobot. The camera 7 provides images of the detected lesion 1, but in particular of the laser irradiation area, which are transmitted via the RF transmit and receive unit 8 to the computer 13 in real time. In addition to the size and shape of the laser irradiation area, the images contain information on the color, shape and texture of the lesion and areas of the lesion already irradiated. Using image recognition algorithms, the computer is able to assign the position, color, shape and texture features before and after an irradiation to specific lesions (lesion classes, lesion types), which in an advantageous embodiment of the present invention are stored in a library accessible to the computer 13.

The computerized specification or classification of the lesion (lesion type) after it is detected enables the subsequent irradiation process to be optimized in terms of size of the laser irradiation area, irradiation period and laser light frequency. This irradiation process is essentially based on two control loops:

Control loop 1 controls the size of the laser irradiation area and/or the surface power density via the distance of the endorobot 5 from the lesion surface and via the selected laser frequency. Normally, the laser 10 of an endorobot 5 is fitted with a lens similar to laser storage devices (optical disk storage) that allows the optical power to be concentrated onto a minimum area (one micrometer) at a finite distance between endorobot 5 and tissue.

Thus with a lens that is actually rigid, it is possible to vary in a defined (controlled) way the surface power density by means of the distance between laser 10 or endorobot 5 and the lesion 1 to be treated or irradiated. The size of the laser irradiation area 2 is monitored periodically or continuously via the camera 7 of the endorobot 5 and input to a control loop in the computer 13 that adjusts the distance precisely to achieve the optimum surface power density, which basically depends on the type of the lesion 1.

Figure 3A:
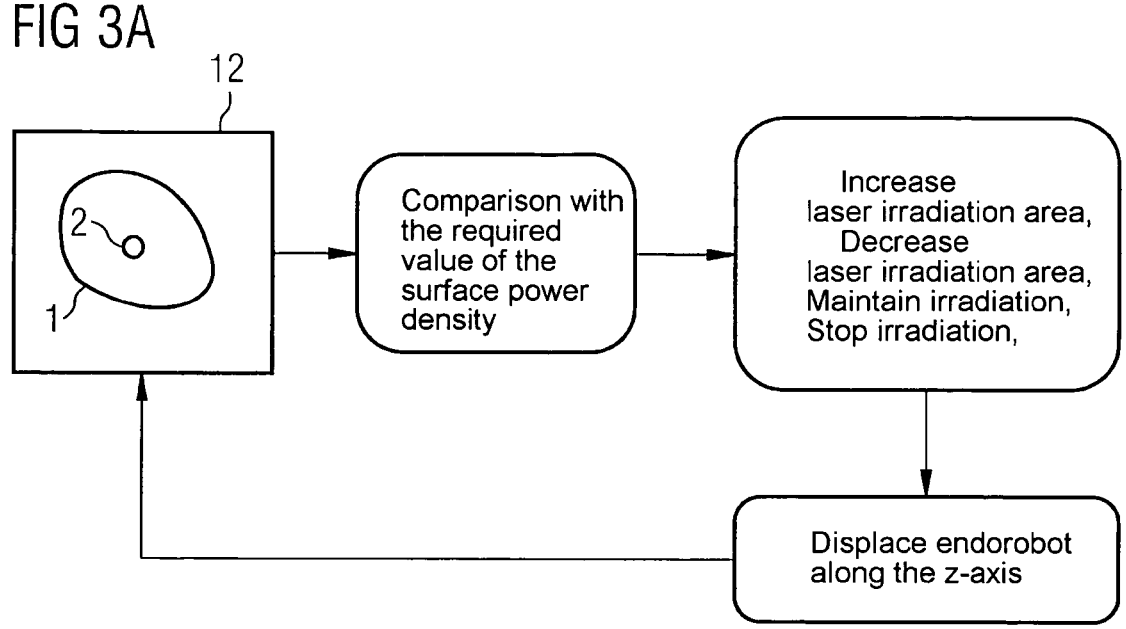
FIG. 3a shows a first control loop relating to the laser irradiation area on the lesion to be coagulated.

The control loop 1 is shown in FIG. 3*a*. The type of the lesion 1 is determined during or after an irradiation with laser light on the basis of shape, size, color, texture by said features being compared by the computer 13 with the corresponding features of different lesion types held in a library. The lesion type is linked to a required value of the surface power density, which can be adjusted by increasing or decreasing the laser irradiation area but also by maintaining or stopping the irradiation. The adjustment is computerized according to an embodiment of the invention.

The laser irradiation surface 2 is normally many times smaller than the lesion 1 itself. In order to still irradiate the whole lesion 1, possibly including the border, automatically or under computer control, another second control loop is necessary which causes the entire lesion 1 (possibly including border) to be scanned by the laser beam.

Figure 3B:
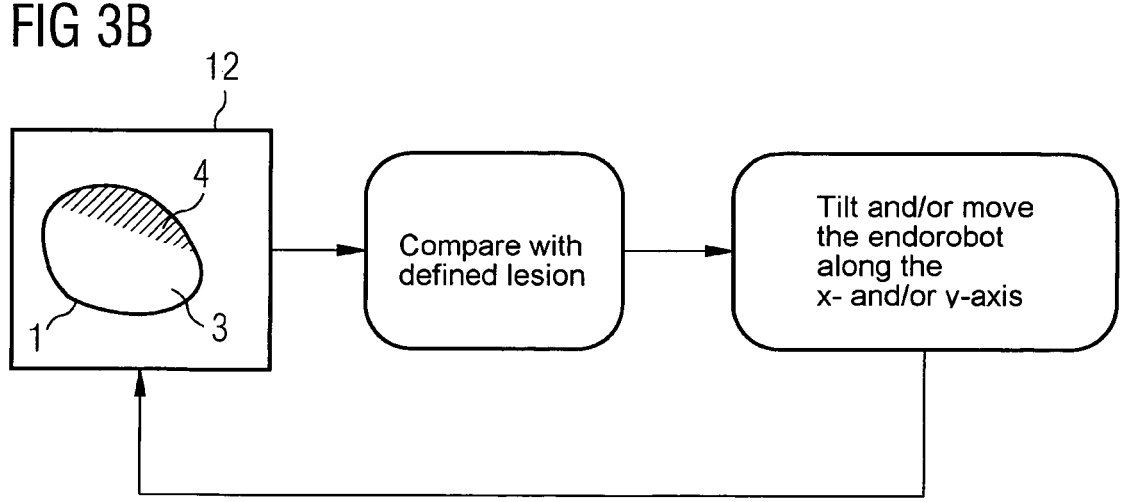
FIG. 3b shows a second control loop relating to the two-dimensional scanning of the surface to be coagulated.

Such a second control loop is shown in FIG. 3*b*. The camera 7 of the endorobot 5 detects continuously or periodically the lesion surface 1 of the diseased organ 12. The transmit and receive unit 8 of the endorobot 5 transmits the camera images to the computer 13, which uses image processing algorithms to detect already-irradiated areas 4 of the lesion, and directs the laser beam onto lesion areas not yet irradiated and onto a border-shaped edge region by tilting or moving the endorobot 5 along the X- and/or Y-axis via the magnetic-field steering system.

Combining both control loops (control loop 1—FIG. 3*a* and control loop 2—FIG. 3*b*) enables an automated and optimized lesion-specific irradiation process, which, in combination with a similarly computerized, automated lesion-detection process, allows a multiplicity of lesions to be coagulated in the shortest possible time.

In different (advantageous) embodiments of the invention, it shall also be possible, amongst other things, for the user to intervene in the automated, computerized action in various ways at different times. The following embodiments include:
1. The user steers the endorobot from lesion to lesion and initializes each irradiation process.
2. The user specifies, possibly via menu selection on the computer, the surface power density curve during the irradiation process.
3. The user decides on the basis of a change in feature (e.g. color change) of the irradiated lesion, whether the irradiation has already had sufficient effect or whether continuing with the previous or modified irradiation parameters (laser irradiation area, frequency, irradiation period) is necessary.
4. Segmentation of the lesion to be irradiated is performed on the computer screen by the user prior to the respective automated irradiation run.

In general it is advantageous, in particular also for safety reasons, to configure the automation of lesion detection and irradiation in such a way that it is possible for the user to plan and/or intervene in all phases of the computerized action.

To summarize, one can say that for the often very large number of lesions in the gastrointestinal tract, automation of lesion detection and lesion irradiation (coagulation) meets a long-held requirement of doctors.

The method and system according to an embodiment of the invention may find an application, as already mentioned several times, in the area of the gastrointestinal tract, in particular of the small intestine. Here, however, the common problem arises that the endorobot is fixed so much by the intestinal wall that it can only be rotated with great difficulty if at all by external magnetic fields (magnetic-field steering system). In particular, this poses severe limitations on the control loop 2.

Another aspect of an embodiment of the present invention therefore involves designing or arranging the laser suitable for ablation in the endorobot in such a way that movement of the endorobot is not the only way of adjusting the laser beam, but the laser beam can be rotated, displaced or even generated at different positions relative to the endorobot. The same control loops of image recognition and control signals, as described above (FIGS. 3*a* and 3*b*), shall be used in this case.

According to an embodiment of the invention, the therapeutic laser shall therefore either be mounted allowing movement relative to the endorobot so that the laser beam can be oriented onto the target tissue without having to move or tilt the endorobot itself, or as an alternative to orientation of the laser, a screen or lens inside the endorobot shall be moved under control relative to the endorobot so that a corresponding movement of the laser beam occurs relative to the endorobot. A further third option would be to arrange a three-dimensional laser (diode) array inside the endorobot, the laser beam being generated solely by actuation of those lasers that have the best impact on the target tissue.

Any miniaturizable electromechanical mechanisms known in the art can be used to achieve a mobility and three-dimensional orientation as described in the first two options according to an embodiment of the invention; motors, movable membranes, shape memory alloys, electrically contractile polymers, piezo-actuators etc. are conceivable here. Even the existing magnetic-field steering system can be used to orientate the laser relative to the endorobot by flexible suspension and rigid coupling of the laser to a (bar) magnet or magnetizable material, which must not be confused with the bar magnets of the endorobot steering device.

The external magnetic fields can be adjusted so that the laser is steered into a given direction by way of the coupled magnet. Here, either the endorobot itself is fixed e.g. by the intestinal wall in such a way that it does not experience any change in position by the steering magnetic field, or the mass or the inertia of the coupled laser magnet system is so much lower than that of the endorobot that a far weaker magnetic field than is necessary to steer the endorobot is sufficient to steer the laser in order to adjust the laser.

It should be mentioned that the steering mechanisms described are not limited to the laser of the endorobot, but other components of the endorobot (e.g. the video camera, other sensors or means of treatment) can also be moved and oriented relative to the endorobot capsule by way of the described mechanisms.

In addition, one should note that control loop 1 and control loop 2 need not necessarily be associated with the transmission of signals from within the body to a computer outside the endorobot. The image processing and control of the endorobot and/or the laser beam could also be performed completely by a processor integrated in the endorobot. The combination of a computer outside the patient with a computer integrated in the endorobot may also be used.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automated localization of lesions in the gastrointestinal tract for treatment using laser light from an endorobot, comprising:

recording surface images of the gastrointestinal tract using a camera of the endorobot;
    transmitting the surface images to a computer;
    analyzing the surface images on the basis of lesion-specific features with regard to lesions to be irradiated;
    computing control signals on the basis of a detected lesion;
    transmitting the control signals to at least one of an endorobot steering device and a laser system located in the endorobot; and
    adjusting a computed laser-beam orientation and size of the laser irradiation area by at least one of the endorobot steering device and the laser system, on the basis of the control signals; wherein
        movement of the laser beam is effected by a magnetic-field steering system, in which the laser is coupled to at least one of a movable magnet and magnetizable material that is not used for navigation of the endorobot and that is capable of being at least one of tilted and displaced by applying an external magnetic field.

2. The method as claimed in claim 1, wherein a controlled irradiation of the detected lesion is performed comprising:

irradiating, using the laser of the endorobot, the lesion detected by the computer on the basis of lesion-specific features;
    measuring current lesion-specific features of the irradiated area by the camera, after switching off the laser;
    calculating the size of the laser irradiation area, using the computer, on the basis of the measured current lesion-specific features;
    setting up the calculated size of the laser irradiation area by positioning the endorobot orthogonally to the lesion surface;
    irradiating, continuous or pulsed, the lesion surface; and
    measuring and monitoring the size and the current lesion-specific features of the laser irradiation area on the lesion surface.

3. The method as claimed in claim 2, wherein the size of the laser irradiation area is varied as a function of the measured current lesion-specific features of the laser irradiation area on the lesion surface by adjusting the distance of the endorobot from the lesion surface.

4. The method as claimed in claim 1, wherein the size of the laser irradiation area is varied as a function of the measured current lesion-specific features of the laser irradiation area on the lesion surface by adjusting the distance of the endorobot from the lesion surface.

5. The method as claimed in claim 1, wherein the size of the laser irradiation area is varied as a function of the measured current lesion-specific features of the laser irradiation area on the lesion surface by varying the laser system.

6. The method as claimed in claim 1, wherein the lesion-specific features concern the color, the shape and the texture of a specific lesion.

7. The method as claimed in claim 1, wherein the lesion-specific features are compared with lesion features in a library at least one of accessible to the computer and in the computer.

8. The method as claimed in claim 1, wherein the irradiation with laser light is at least one of interruptable and stoppable at least one of any time and at periodic intervals, in order to measure the size of the laser irradiation area and to measure the lesion-specific features.

9. The method as claimed in claim 1, wherein the recording of surface images, the transmission to the computer and the analysis by the computer are advantageously performed continuously.

10. The method as claimed in claim 9, wherein at least one of the transverse displacement of the laser beam in the XY-plane and the tilting of the laser beam relative to the Z-axis is performed by three-dimensional orientation of the laser relative to the endorobot.

11. The method as claimed in claim 10, wherein the three-dimensional orientation of the laser relative to the endorobot is performed by miniaturized electromechanical mechanisms.

12. The method as claimed in claim 11, wherein the miniaturized electromechanical mechanisms include at least one of movable membranes, shape memory alloys, electrically contractile polymers, and piezo-actuators.

13. The method as claimed in claim 11, wherein an orientation of additional components of the endorobot is performed.

14. The method as claimed in claim 10, wherein the movement of the laser beam is effected by moving a screen.

15. The method as claimed in claim 10, wherein the movement of the laser beam is effected by actuating selected laser diodes of a 3D laser diode array integrated in the endorobot.

16. The method as claimed in claim 10, wherein an orientation of additional components of the endorobot is performed.

17. The method as claimed in claim 1, wherein the whole lesion surface is irradiated with a defined surface power density of the laser by at least one of transverse displacement of the laser beam in the XY-plane and by tilting the laser beam relative to the lesion-endorobot connecting line by suitable movement of the endorobot in combination with the supervised positioning in the Z-direction of the endorobot.

18. The method as claimed in claim 17, wherein the surface power density is defined by the computer over time as a function of the type of the lesion.

19. The method as claimed in claim 18, wherein at least one of the transverse displacement of the laser beam in the XY-plane and the tilting of the laser beam relative to the Z-axis is performed by three-dimensional orientation of the laser relative to the endorobot.

20. The method as claimed in claim 17, wherein at least one of the transverse displacement of the laser beam in the XY-plane and the tilting of the laser beam relative to the Z-axis is performed by three-dimensional orientation of the laser relative to the endorobot.

21. A system for automated localization of lesions in the gastrointestinal tract for treatment using laser light from an endorobot, the system comprising:

means for recording surface images of the gastrointestinal tract using a camera of the endorobot;
    means for transmitting the surface images to a computer;

means for analyzing the surface images on the basis of lesion-specific features with regard to lesions to be irradiated;

means for computing control signals on the basis of a detected lesion;

means for transmitting the control signals to at least one of an endorobot steering device and a laser system located in the endorobot; and means for adjusting a computed laser-beam orientation and size of the laser irradiation area by at least one of the endorobot steering device and the laser system, on the basis of the control signals; wherein movement of the laser beam is effected by a magnetic-field steering system, in which the laser is coupled to at least one of a movable magnet and magnetizable material that is not used for navigation of the endorobot and that is capable of being at least one of tilted and displaced by applying an external magnetic field.

22. The system as claimed in claim 21, wherein the means for computing is located outside the patient under examination.

23. The system as claimed in claim 21, wherein the means for computing is integrated inside the endorobot.

24. The system as claimed in claim 21, further comprising:

means for irradiating, using the laser of the endorobot, the lesion detected by the computer on the basis of lesion-specific features;

means for measuring current lesion-specific features of the irradiated area by the camera, after switching off the laser;

means for calculating the size of the laser irradiation area, using the computer, on the basis of the measured current lesion-specific features;

means for setting up the calculated size of the laser irradiation area by positioning the endorobot orthogonally to the lesion surface;

means for irradiating, continuous or pulsed, the lesion surface; and means for measuring and monitoring the size and the current lesion-specific features of the laser irradiation area on the lesion surface.

25. The system as claimed in claim 24, wherein the means for computing is located outside the patient under examination.

26. The system as claimed in claim 24, wherein the means for computing is integrated inside the endorobot.

27. A system for automated localization of lesions in the gastrointestinal tract using laser light from an endorobot, the endorobot recording surface images of the gastrointestinal tract, comprising:

means for transmitting the recorded surface images;

means for analyzing the surface images on the basis of lesion-specific features with regard to lesions to be irradiated and for computing control signals on the basis of a detected lesion;

means for transmitting the control signals to a device located in the endorobot; and means for adjusting a computed laser-beam orientation and size of a laser irradiation area on the basis of the control signals; wherein the movement of the laser beam is effected by a magnetic-field steeling system, in which the laser is coupled to at least one of a movable magnet and magnetizable material that is not used for navigation of the endorobot and that is capable of being at least one of tilted and displaced by applying an external magnetic field.

28. The system of claim 27, wherein the means for analyzing and for computing includes a computer device.

29. The system as claimed in claim 28, wherein the computer device is located outside the patient under examination.

30. The system as claimed in claim 28, wherein the computer device is integrated inside the endorobot.

31. A method for automated localization of lesions in the gastrointestinal tract for treatment using laser light from an endorobot, the method comprising:

recording surface images of the gastrointestinal tract using a camera of the endorobot;

analyzing the recorded surface images based on lesion-specific features of lesions to be irradiated;

adjusting, in response to control signals generated based on a detected lesion, a computed laser-beam orientation and size of the laser irradiation area by at least one of an endorobot steering device and a laser system; wherein movement of the laser beam is effected by a magnetic-field steering system including at least one of a movable magnet and magnetizable material that is not used for navigation of the endorobot.

32. The method of claim 31, wherein the laser is capable of being at least one of tilted and displaced by applying an external magnetic field.

* * * * *